United States Patent [19]

Langensee

[11] Patent Number: 5,072,063
[45] Date of Patent: Dec. 10, 1991

[54] PROCESS FOR REARRANGING ALLYLIC GEMINAL DIHALOGEN COMPOUNDS

[75] Inventor: Peter Langensee, Stade, Fed. Rep. of Germany

[73] Assignee: DowElanco, Indianapolis, Ind.

[21] Appl. No.: 462,523

[22] Filed: Jan. 9, 1990

[51] Int. Cl.$^5$ .............................................. C07C 21/04
[52] U.S. Cl. .................................................... 570/236
[58] Field of Search ......................................... 570/236

[56] References Cited

U.S. PATENT DOCUMENTS 2,846,483 8/1958 Taplin, III .
4,319,062 3/1982 Boozalis et al. .

OTHER PUBLICATIONS

V. D. Izmailov et al., *Khim. Khim. Tekhnol.*, 17, 562–564 (1974), (*Chem. Abs.*, 81, 24873k (1974).
J. R. Shelton et al., *J. Org. Chem.*, 23, 1876–1880 (1958).
*Beilsteins Handbuch Der Organischen Chemie*, Erster Band, p. 199.
D. Seyferth et al., *J. Organometallic Chem.*, 90, 173–184 (1975).
D. Seyferth et al., *J. Am. Chem. Soc.*, 99, 5317–5330 (1977).

*Primary Examiner*—Howard T. Mars
*Attorney, Agent, or Firm*—D. Wendell Osborne

[57] ABSTRACT

Cis- and trans-1,3-dichloropropenes and their homologs and 1,3-dibromopropenes can be prepared by isomerizing the corresponding 3,3-dihalopropene or homolog thereof in a simple, high yield process by contacting the latter with an effective silica, alumina, or zeolite catalyst. Thus, a mixture of cis- and trans-1,3-dichloropropenes is produced in good yield and with good selectivity when a mixture of 3,3-dichloropropene with other chlorinated hydrocarbons, principally 1,2-dichloropropane, is contacted with an acidic activated alumina catalyst at a temperature of about 100° C.

17 Claims, No Drawings

PROCESS FOR REARRANGING ALLYLIC GEMINAL DIHALOGEN COMPOUNDS

BACKGROUND OF THE INVENTION

The present invention relates to a process for preparing a 1,3-dihaloalkene compound, such as a 1,3-dichloropropene or a homolog thereof, from the corresponding allylic geminal dihalide compound, such as a 3,3-dihalopropene or homolog thereof, by treatment with an alumina, silica, or zeolite catalyst.

Many different methods for producing 1,3-dichloropropenes have been suggested, for example, by reacting 1,2-dichloropropane with a gas containing oxygen in the presence of a catalyst containing $CuCl_2$, LiCl and $ZnCl_2$ at 470° C. to 490° C.: by dehydrochlorination of 1,2,3-trichloropropane in the presence of oxygen or a halogen; by contacting 1,2-dichloropropane with chlorine to effect both chlorination and dechlorination reactions; or by mixing 1,2-dichloropropane with allyl chloride and/or 1-chloropropene and reacting with chlorine at high temperature. However, all these processes are rather complicated, energy-consuming an/or inconvenient.

1,3-Dichloropropenes have been prepared by isomerization of 3,3-dichloropropene in the presence of hydrogen chloride. This isomerization is also known from Japanese Patent No. 80-69,523 to take place in the presence a catalytic amount of a zinc, iron, copper, tin, titanium or vanadium salt. The isomerization catalyst is suspended in the reaction mixture and the reaction is carried out at a temperature between 0° C. and 200° C. This disclosed process of rearranging 3,3-di-chloropropene to 1,3-dichloropropenes is, however, rather inconvenient because the finely suspended catalyst is difficult to remove from the reaction mixture after completion of the rearrangement process.

The production of 1,3-dichloropropenes and their homologs starting from 3,3-dichloropropene and its homologs is advantageous because 3,3-dichloropropene and its homologs do not have a significant commercial use and are available. 3,3-Dichloropropene itself is produced as a by-product in the important commercial process of producing allyl chloride by chlorinating propylene. In the past, the 3,3-dichloropropene produced has usually been incinerated.

It is known in the art, however, that both the cis and trans isomers of 1,3-dichloropropene have many useful properties. For example, it is known from published German Patent Application No. 1,210,618 that these compounds are useful as nematocides. They are also useful as insecticides. These and other compounds produced by the invention are also known to be useful as monomers in the production of plastics and resins and as chemical intermediates. Because of these useful properties, much effort has been spent to produce such compounds in the recent years.

Therefore, it remains highly desirable to provide a simple and high yield process for producing 1,3-dihalopropenes and their homologs from 3,3-dihalopropenes and their homologs.

SUMMARY OF THE INVENTION

Surprisingly, it has been found that 1,3-dichloropropenes, such as cis- and trans-1,3-dichloropropene, and their homologs and 1,3-dibromopropenes can be prepared by isomerizing the corresponding 3,3-dihalopropene or homolog thereof in a simple, high yield process by contacting the latter with an effective silica, alumina, or zeolite catalyst. The invention includes a process for preparing a dihaloalkene compound of Formula I or Formula II

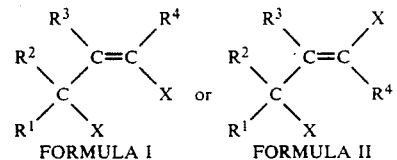

wherein
X represents chloro or bromo and
$R^1$, $R^2$, $R^3$, and $R^4$ independently represent hydrogen or a $C_1$–$C_3$ alkyl group, with the proviso that when X represent bromo each of $R^1$, $R^2$, $R^3$, and $R^4$ represents hydrogen or a mixture thereof, which process comprises contacting a dihaloalkene compound of Formula III

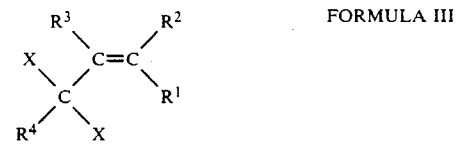

wherein
X represents chloro or bromo and $R^1$, $R^2$, $R^3$, and $R^4$ independently represent hydrogen or a $C_1$–$C_3$ alkyl group, with the proviso that when X represents bromo each of $R^1$, $R^2$, $R^3$, and $R^4$ represents hydrogen with an effective catalyst selected from the group consisting of an alumina, a silica, and a zeolite at an effective temperature of from about 0° C. to about 130° C. The preparation of cis- and/or trans-1,3-dichloropropene by isomerization of 3,3-dichloropropene is of special interest. Acidic, activated aluminas are preferred catalysts.

DETAILED DESCRIPTION OF THE INVENTION

The dihaloalkene starting materials for the present process are those of Formula III wherein X represents chloro and $R^1$, $R^2$, $R^3$, and $R^4$ independently represent hydrogen or a $C_1$–$C_3$ alkyl group or wherein X represents bromo and each of $R^1$, $R^2$, $R^3$, and $R^4$ represents hydrogen. Compounds of Formula III wherein X represents chloro and $R^1$, $R^2$, $R^3$, and $R^4$ independently represent hydrogen or a methyl group are preferred starting materials as are compounds of Formula III wherein each of $R^1$, $R^2$, $R^3$, and $R^4$ represents hydrogen. 3,3-Dichloropropene is an especially preferred starting material. The dichloroalkene products of the process are those of Formulas I and II wherein X represents chloro and $R^1$, $R^2$, $R^3$, and $R^4$ independently represent hydrogen or a $C_1$–$C_3$ alkyl group or wherein X represents bromo and each of $R^1$, $R^2$, $R^3$, and $R^4$ represents hydrogen. Compounds of Formulas I and II wherein X represents chloro and $R^1$, $R^2$, $R^3$, and $R^4$ independently represent hydrogen or a methyl group are preferred products as are compounds wherein each of $R^1$, $R^2$, $R^3$, and $R^4$ represents hydrogen. 1,3-Dichloropropene in either the cis (Z) or trans (E) configuration (Formulas I and II wherein X represents chloro and each of $R^1$, $R^2$, $R^3$, and $R^4$ represents hydrogen, respectively) is an especially preferred product. The compounds of Formula I and II are geometric isomers differing only by the geometry around the double bond of the compound. The process typically produces some of both of these geometric isomers. Generally, the trans (E) isomer of Formula II predominates. The invention includes the production of either of these isomers or any mixture thereof.

The term alkyl as used herein includes both straight chain and branched chain alkyl groups. Typical alkyl groups are methyl, ethyl, propyl, and 1-methyl-ethyl.

The process of the present invention can be carried out neat; i.e., without the use of a reaction diluent. Preferably, however, a suitable reaction diluent is mixed with the compound of Formula III. A suitable reaction diluent is a liquid that is chemically inert in the system: i.e., it does not significantly react with the catalyst, the starting material or the products, does not deactivate the catalyst, and does not significantly decompose under the reaction conditions. Generally, both the starting materials and the products of the process are soluble in the diluent at the temperature employed in the process.

The compounds most generally employed as diluents are chlorinated hydrocarbons. Preferred chlorinated hydrocarbons are those having a boiling point that allows for reaction in the liquid phase at an elevated temperature, for example, at a temperature of more than about 50° C., preferably of up to about 130° C. Such compounds are generally chlorinated hydrocarbons having 1 to 6 carbons atoms. Examples of the preferred diluents include saturated chlorinated hydrocarbons, such as carbon tetrachloride, chloroform, 1,2-dichloroethane, 1,1,1-trichloroethane, 1,1,2-trichloroethane, 1,1,1,2-tetrachloroethane, 1,2-dichloropropane, 2,2-dichloropropane, 1,3-dichloropropane, 1,1,2-trichloropropane, 1,1,3-trichloropropane, 1,2,3-trichloropropane, 1,1,2,3-tetrachloropropane, 1,1,1,2-tetrachloropropane, 2,3-dichlorobutane, and 1,2,2,3-tetrachlorobutane. A particularly preferred reaction diluent of this type is 1,2-dichloropropane. Other examples of preferred diluents include unsaturated chlorinated hydrocarbons, such as 1,2-dichloroethene, trichloroethene, tetrachloroethene, 1,2-dichloropropene, 2,3-dichloropropene, 1,3-dichloropropene, 1,1,3-trichloropropene, and 1,2-dichlorobenzene. Such reaction diluents, however, should not have two geminal allylic chlorine substituents. 1,3-Dichloropropenes in either or both of the cis and trans configurations are preferred diluents as well as preferred products.

Polar, protic reaction diluents, such as water and alcohols, non-polar hydrocarbon reaction diluents, such as hexane and heptane, and reaction diluents which might react with the reactants, products and/or intermediates formed during the reaction, such as benzene or toluene, generally are not useful for the process of the present invention.

The starting material dichloroalkenes of Formula III and methods of producing them are generally known in the art. 3,3-Dichloropropene is a by-product resulting from the production of allyl chloride by chlorination of propylene. Other dichloroalkenes of Formula III can be prepared by reduction or alkylation of 3,3-dichloroallyl lithium or a homolog thereof as taught in *Journal of the American Chemical Society*, 99, 5317-5330 (1977). Compounds of either Formula IV or V

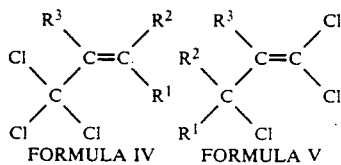

wherein $R^1$, $R^2$, and $R^3$ independently represent hydrogen or $C_1$-$C_3$ alkyl can be used starting materials to obtain the 3,3-dichloroallyl lithium or a homolog thereof required for this preparation. These compounds are generally known in the art or can be prepared by methods known in the art. 3,3-Dibromopropene has been prepared by dehydration of 3,3-dibromo-1-propanol.

The chlorination of propylene to produce allyl chloride is described in U.S. Pat. No. 4,319,062. The by-product stream from this process that is obtained as material of intermediate boiling point after removing the lower boiling fractions containing the allyl chloride and the higher boiling fractions containing most of the cis- and trans-1,3-dichloropropenes by distillation contains a variety of chlorinated propanes and propenes of which generally between about 10 and 20 percent by total weight is 3,3-dichloropropene. Other by-products of the process include 2,3-dichloropropene, 2,2-dichloropropane, cis- and trans-1,3-dichloropropenes, 1,2-dichloropropane and many other related species. Usually, 1,2-dichloropropane is present as a major component, often amounting to approximately 50 percent to 85 percent by weight. Typically, this compound is present to the extent of about 60 to 75 percent of the stream by weight. 1,3-Dichloropropenes are other principal components of the mixture. 1,2-Dichloropropane and 1,3-dichloropropenes are preferred reaction diluents for the process of the present invention. Accordingly, the rearrangement of 3,3-dichloropropene to 1,3-dichloropropenes by means of the present invention can be carried out on this by-product stream without first recovering the 3,3-dichloropropene from it. Accordingly, the process of the present invention provides an opportunity to produce 1,3-dichloropropenes in a high yield within a relatively short time and to eliminate an undesired compound in the by-product stream resulting from the production of allyl chloride. This is a preferred application of the process.

The process requires a heterogeneous, solid catalyst employed in an effective amount. Suitable catalysts include aluminas, silicas, and zeolites. Aluminas, silicas, and zeolites that have acidic sites are preferred. Such acidic sites can be either or both of the Lewis and Bronsted types. Suitable catalysts usually have relatively large surface areas in the range of about 50 to about 700 meters$^2$/gram (m$^2$/g) and contain very little water. These substances are naturally occurring or are synthetic. Synthetic forms are generally preferred.

Aluminas are often preferred as catalysts. Most natural and synthetic types of alumina are useful as catalysts but acidic, activated aluminas are generally preferred. Aluminas of this type are characterized by a strong capability of adsorbing organic compounds and by having a relatively large surface area. They are generally composed primarily of $\gamma$-alumina, have essentially no water of hydration, and possess acidic sites on the surface.

Suitable aluminas include MERCK-Schuchardt acidic aluminum oxide 90 (activity level I, 0.063 to 0.2 millimeters (mm) diameter); Riedel-de Haen acidic Super Activity (I) aluminum oxide S (pH of aqueous slurry about 4.5, surface area about 200 m$^2$/g, pour density about 0.9 g, 70-290 ASTM mesh (50 to 210 micrometers ($\mu$m) diameter): Rhone-Poulenc Inc. alumina SES-300 or SAS-350 (surface area of 300 to about 450 m$^2$/g, total pore volume 0.48-0.52 milliliters/g (ml/g), bulk density 0.71-0.73 g/ml, mercury pore volume 0.4 to about 0.5 ml/g, with at least 19 percent of the pores being greater that about 0.1 $\mu$m in diameter) as 6 to 8 mm diameter spheres; Norton Chemical Process Products alumina grade SA-6275: ICN acidic alumina (pH of aqueous slurry about 4.5, surface area about 200 m$^2$/g, pour density about 0.9 g, 50 to 200 $\mu$m diameter particles): ICN alumina of from Super Activity I to activity level II–III (powder with surface area of about 200 m$^2$/g); Aldrich acidic alumina (pH of aqueous slurry 4.0–5.0, surface area about 155 m$^2$/g); Sep Pak basic alumina; Harshaw aluminas Al-3945, AL-3952, Al-4126, and super acid-1 3998 as 1.6 mm diameter exudates or crushed; Harshaw phosphoric acid doped alumina P-0620-T as 3.2 mm pellets; Alpha Products gamma alumina 99 percent as 3.2 mm pellets; EM Science alumina AX0610-3 as as 3.2 mm pellets; Martinswerke GmbH activated aluminum oxide Compalox AN/V-801, and K-10 montmorillonite clay available from Aldrich Chemical Company. Many other suitable aluminas are commercially available.

Silicas can also be used as catalysts. Acidic silica gels are preferred. Acidic silica gels are characterized by a strong capability of adsorbing organic compounds, having acidic sites on the surface, and having a relatively large surface area. One useful type of silica is silica gel 60 which has a particle size of about 40 to 63 $\mu$m diameter and is obtainable from MERCK-Schuchardt.

Furthermore, zeolites (also called molecular sieves) are useful as catalysts. Preferred classes of zeolites include those characterized by having relatively large diameter pores, having a relatively large surface area, and having been made acidic by hydrogen ion exchange or by thermolysis of the ammonium ion form or otherwise having acidic sites on the surface. Acidic forms of commercially available zeolites A, X and Y are often especially preferred. Acidic forms of zeolite Y are especially preferred. Examples of suitable zeolites include the materials commercially available from MERCK-Schuchardt as one nanometer nominal pore diameter molecular sieves and from Union Carbide as molecular sieve 13X (type X, octahedral crystal form, one nanometer (nm) nominal pore diameter) available as powder or as 1.6 or 3.2 mm pellets.

Mixtures of different above-mentioned catalysts, for example, blends of alumina and silica, such as a blend of 5 to 30 weight percent of silica and 95 to 70 weight percent of alumina are also useful. Additionally, other materials, such as fillers, binders, flow aids, and the like, can be present in the catalyst.

The alumina, silica, and zeolite catalysts can be employed in the form of solid particulates having a diameter of from about 1 $\mu$m to about 30 mm, preferably from about 10 $\mu$m to about 10 mm, and more preferably from about 100 $\mu$m to about 6 mm. These materials are typically made by precipitation methods that produce particles of less than about 100 $\mu$m diameter. The small particles obtained can be formed into larger agglomerates by pressure or by adding binders, such as clays, before or during the drying operation as is known in the art. Catalysts that are agglomerates composed of many smaller particles and are, therefore, larger in diameter are often advantageously employed in the process because of their ease of handling, especially their ease of removal from the product stream. The agglomerated catalysts may be in the form of pellets, exudates, spheres, tablets, granules, or other shaped form.

The ratio between the compound of Formula III and the catalyst can vary within broad ranges limited only by the requirement that an effective amount of catalyst be present and by practicality. The minimum effective amounts and optimum amounts of a catalyst are a function of the specific compound of Formula III employed, the specific catalyst employed, the operating conditions, such as the temperature and pressure, and the geometry and mode of operation of the reactor employed. The minimum effective amount of catalyst is generally less than about 0.1 percent, and often below about 0.01 percent and the optimum weight ratio between the catalyst and the total amount of compound of Formula III employed is generally between about 1:1 to 1:1,000. The optimum amount for any situation can readily be determined by range finding experiments using the disclosure herein and known chemical principles.

The process of the present invention can be carried out batchwise. However, it is a major advantage that the process can also be carried out continuously. Preferably, the continuous process is a fixed bed process wherein the compound of Formula III is allowed to flow through a fixed bed containing one or more of the above mentioned catalysts. Fluidized bed reactors can also be employed.

The process of the present invention is generally carried out at a temperature of from about 0° C. to about 130° C., preferably from about 20° C. to about 120° C., more preferably from about 50° C. to about 110° C. It is highly advantageous that the process of the present invention can be carried out at relatively low temperatures. Higher temperatures are contraindicated because the compounds of Formulas I and II produced, such as cis- and trans-1,3-dichloropropene, start to decompose in the presence of the catalysts at temperatures above about 130° C. Pressure is not a critical variable and any convenient pressure is suitable for the process. Preferably, the reaction is carried out at ambient pressure or at a superatmospheric pressure up to about 1500 kiloPascals (kPa). The combination of temperature and pressure is preferably selected so that substantially all components of the reaction mixture remain in the liquid state during the process.

The reaction time depends mainly on the specific starting material, the temperature, the catalyst, and the reactor employed in the process. If the process is carried out batchwise, the reaction is generally complete within about 0.5 to about 8 hours, in most of the cases between about 1.5 and about 4 hours. When the process is carried out continuously, a residence time of the compound of Formula III in the fixed bed containing the catalyst of about 1 to about 300 minutes is generally sufficient. In most cases a residence time of about 2 to about 180 minutes and in many cases a residence time of only about 2 to about 120 minutes is sufficient and is preferred.

The process of the present invention can be carried out batchwise in a simple manner by stirring the compound of Formula III, optionally mixed with an inert solvent, with an above-mentioned catalyst. Most preferably, a by-product stream resulting from the production of allyl chloride by the chlorination of propylene is stirred with the catalyst. After completion of the rearrangement process, the catalyst is separated from the reaction mixture by sedimentation, centifugation, or filtration.

The process of the present invention is preferably carried out continuously by passing a compound of Formula III, optionally mixed with a reaction diluent, through a tubular reactor containing a suitable catalyst. In a specifically preferred embodiment of the invention, a by-product stream resulting from the production of allyl chloride by the chlorination of propylene is passed through such a reactor.

When producing 1,3-dichloropropenes according to the process of the present invention, a mixture of cis- and trans-1,3-dichloropropenes (compounds of Formulas I and II wherein X represents chloro and each of $R^1$, $R^2$, $R^3$, and $R^4$ represents hydrogen, respectively) is obtained. Surprisingly, between 10 and 20 percent of cis-1,3-dichloropropene and between 80 and 90 percent of trans-1,3-dichloropropene are obtained, based on the total yield of 1,3-dichloropropenes obtained. After completion of the reaction, the cis- and trans-1,3-dichloropropenes can be separated from the other components of the reaction mixture, for example, by distillation. Cis- and trans-1,3-dichloropropenes can be separated from each other by known methods, for example, by distillation, due to their different physical properties.

The conversion of 3,3-dichloropropene to 1,3-dichlorpropenes in the process and the selectivity of the reaction to produce cis- and trans-1,3-dichloropropenes depends on various factors such as the reaction conditions and the amount and types of catalyst employed. When employing optimized conditions, a molar conversion of 3,3-dichloropropene of more than 90 percent can be attained and the selectivity of converted 3,3-dichloropropene to 1,3-dichloropropenes (total) is generally more than 90 percent, in most cases about 95 percent or more.

The following examples illustrate the present invention and should not be construed to limit the scope of the invention. Unless otherwise mentioned all parts and percentages are by weight.

EXAMPLE 1

Production of 1,3-Dichloropropenes by Isomerization of 3,3-Dichloropropene with Alumina Catalyst—Continuous Reactor A solution of 3,3-dichloropropene in a mixture of chlorinated hydrocarbons of which 1,2-dichloropropane was predominant, which solution was obtained as a by-product stream resulting from the production of allyl chloride by chlorination of propylene, was passed through a glass column which was filled with an acidic type alumina catalyst commercially available from MERCK-Schuchardt under the designation: MERCK alumina 90/Brockman activity I/acidic/70 to 230 mesh ASTM (63 to 210 μm diameter). The column had a length to diameter ratio of 5 to 1. The weight ratio between the amount of catalyst in the column and the amount of by-product stream passed through the column was 1 to 10. The temperature of the by-product stream was about 20° C. and its residence time in the column was 2 to 3 minutes. The compositions of the mixture fed to the reactor and of the effluent were analyzed by gas chromatography and the results are given in Table 1. The conversion of 3,3-dichloropropene to 1,3-dichloropropenes (sum of cis and trans isomers) was found to be 69.3 percent and the selectivity was found to be 95 percent.

EXAMPLE 2

Production of 1,3-Dichloropropenes by Isomerization of 3,3-Dichloropropene with Alumina Catalyst—Batch Reactor To 50 parts of a solution of 3,3-dichloropropene in a mixture of chlorinated hydrocarbons of which 1,2-dichloropropane was predominant, which solution was obtained as a by-product stream resulting from the production of allyl chloride by chlorination of propylene, was added 10 parts of molecular sieve 1.0 nm commercially available from MERCK-Schuchardt. The mixture was stirred at a temperature between 80° C. and 90° C. for 2 hours. The compositions of the by-product stream employed and of the reaction mixture after completion of the reaction were determined by gas chromatographic analysis and the results are given in Table I. The conversion of 3,3-dichloropropene to 1,3-dichloropropenes (sum of cis and trans isomers) was found to be 91.0 percent and the selectivity was found to be 94 percent.

TABLE I

| Components of Mixtures | Example 1 | | Example 2 | |
| --- | --- | --- | --- | --- |
| | Feed[1] | Prod.[1] | Feed[1] | Prod.[1] |
| 3,3-dichloropropene | 12.8 | 3.9 | 16.2 | 1.5 |
| 1,2-dichloropropane | 67.0 | 67.5 | 70.7 | 72.4 |
| 2,2-dichloropropane | 1.1 | 1.0 | 1.0 | 1.3 |
| 2,3-dichloropropene | 11.9 | 11.9 | 7.6 | 8.1 |
| cis-1,3-dichloropropene | 5.8 | 6.9 | 1.2 | 3.8 |
| trans-1,3-dichloropropene | 0.1 | 7.2 | 0.05 | 11.3 |
| (sum 1,3-dichloropropenes) | 5.9 | 14.1 | 1.05 | 15.1 |

[1]Percent by weight

EXAMPLE 3

Production of 1,3-Dichloropropenes by Isomerization of 3,3-Dichloropropene with Alumina Catalyst in a Continuous Reactor A monel columnar reactor measuring 10.2 cm by 1.82 meter (18:1 length to diameter ratio) was filled with 10.2 kilograms (kg) of Rhone-Poulenc SES-300 grade alumina in a spherical form having a diameter of between 2.38 mm and 3.36 mm (6/8 ASTM mesh). A solution of 3,3-dichloropropene in a mixture of chlorinated hydrocarbons of which 1,2-dichloropropane was predominant, which solution was obtained as a by-product stream resulting from the production of allyl chloride by chlorination of propylene, was heated to 100° C. and passed through the column at the rate of 27.3 kg per hour for about 456 hours. This amounts to a total of about 2500 kg of 3,3-dichloropropene and a ratio of substrate to catalyst of about 250:1. The residence time in the reactor was 38 minutes. The compositions of the by-product stream employed and of the reaction mixture after completion of the reaction were determined by gas chromatographic analysis at various times and the results obtained at 74.5 hours, which are typical, are given in Table II. The conversion of 3,3-dichloropropene to 1,3-dichloropropenes (sum of cis and trans isomers) was found to be 46 percent and the selectivity was found to be 100 percent.

EXAMPLE 4

Production of 1,3-Dichloropropenes by Isomerization of 3,3-Dichloropropene with Alumina Catalyst in a Continuous Reactor The reactor employed in Example 3 was filled with 8.68 kg of Norton Process Chemical Co. SA-6275 grade alumina in the form of about 3.2 mm diameter spheres. A solution of 3,3-dichloropropene in a mixture of chlorinated hydrocarbons of which 1,2-dichloropropane was predominant, which solution was obtained as a by-product stream resulting from the production of allyl chloride by chlorination of propylene, was heated to 100° C. and passed through the column at the rate of 27.3 kg per hour for about 144 hours, 18.2 kg per hour for about 264 hours and 13.6 kg per hour for about 1056 hours. This amounts to a total of approximately 3000 kg of 3,3-dichloropropene and a ratio of substrate to catalyst of approximately 350:1. The residence time in the reactor varied from 38 minutes to about 76 minutes depending on the flow rate. The compositions of the by-product stream employed and of the reaction mixture after completion of the reaction were determined by gas chromatographic analysis at various times and the results obtained at 248 hours (when the flow rate was 18.2 kg per hour and the residence time was 55 minutes) are given in Table II. The conversion of 3,3-dichloropropene to 1,3-dichloropropenes (sum of cis and trans isomers) was found to be 75 percent and the selectivity was found to be 100 percent.

TABLE II

| Components of Mixtures | Example 3 Feed[1] | Example 3 Prod.[1] | Example 4 Feed[1] | Example 4 Prod.[1] |
|---|---|---|---|---|
| 3,3-dichloropropene | 20.3 | 11.0 | 13.9 | 3.5 |
| 1,2-dichloropropane | 70.5 | 69.4 | 61.2 | 60.8 |
| 2,2-dichloropropane | 1.8 | 1.5 | 1.1 | 0.9 |
| 2,3-dichloropropene | — | — | 6.8 | 6.6 |
| cis-1,3-dichloropropene | 7.0 | 9.5 | 15.0 | 16.4 |
| trans-1,3-dichloropropene | 0.1 | 7.6 | 1.5 | 11.0 |
| (sum 1,3-dichloropropenes) | 7.1 | 17.7 | 16.5 | 27.4 |

[1]Percent by weight, at the time specified

What is claimed is:

1. A process for preparing a dihaloalkene compound of the formula

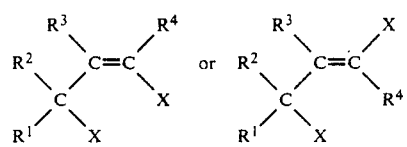

wherein

X represents chloro or bromo and $R^1$, $R^2$, $R^3$, and $R^4$ independently represent hydrogen or a $C_1$–$C_3$ alkyl group, with the proviso that when X represents bromo each of $R^1$, $R^2$, $R^3$, and $R^4$ represents hydrogen or a mixture thereof, which process comprises contacting a dihaloalkene compound of the formula

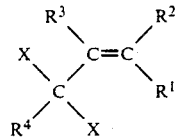

wherein

X represents chloro or bromo and $R^1$, $R^2$, $R^3$, and $R^4$ independently represent hydrogen or a $C_1$–$C_3$ alkyl group, with the proviso that when X represents bromo each of $R^1$, $R^2$, $R^3$, and $R^4$ represents hydrogen in the liquid state with an effective catalyst selected from the group consisting of an alumina, a silica, and a zeolite at an effective temperature of from about 0° C. to about 130° C.

2. A process according to claim 1 wherein each of $R^1$, $R^2$, $R^3$, and $R^4$ in the dichloroalkene compound starting material represents hydrogen.

3. A process according to claim 2 wherein X in the dichloroalkene starting material compound represents chloro; that is, the dichloroalkene starting material compound is 3,3-dichloropropene.

4. A process according to claim 3 wherein the 3,3-dichloropropene starting material compound employed is a component of a by-product stream resulting from the production of allyl chloride by chlorination of propylene.

5. A process according to claim 1 wherein X in the dichloroalkene starting material compound represents chloro and $R^1$, $R^2$, $R^3$, and $R^4$ independently represent hydrogen or methyl.

6. A process according to claim 1 wherein the dichloroalkene compound produced is cis- or trans-1,3-dichloropropene or a mixture thereof.

7. A process according to claim 1 wherein the catalyst is an alumina.

8. A process according to claim 7 wherein the alumina is an acidic, activated alumina.

9. A process according to claim 1 wherein the catalyst is an acidic silica gel.

10. A process according to claim 1 wherein the catalyst is an acidic form of zeolite A, X, or Y.

11. A process according to claim 1 wherein an inert diluent is additionally present.

12. A process according to claim 11 wherein the inert diluent is a chlorinated hydrocarbon or mixture of chlorinated hydrocarbons.

13. A process according to claim 12 wherein the chlorinated hydrocarbon is 1,2-dichloropropane or the mixture of chlorinated hydrocarbons contains 1,2-dichloropropane as a major component.

14. A process according to claim 1 wherein the contacting temperature is between about 20° C. and about 120° C.

15. A process according to claim 14 wherein the contacting temperature is between about 50° C. and about 110° C.

16. A process according to claim 1 carried out in a continuous manner.

17. A process according to claim 1 wherein the starting material dichloropropene compound is 3,3-dichloropropene and a inert chlorocarbon diluent is employed, the mixture of 3,3-dichloropropene and diluent being a by-product stream resulting from the production of allyl chloride by chlorination of propylene, the dichloropropene compound produced is cis- or trans-1,3-dichloropropene or a mixture thereof, the catalyst is an acidic activated alumina, the temperature of the contacting is between about 20° C. and about 120° C. and the process is conducted in a continuous manner.

* * * * *